US011253147B1

(12) United States Patent
Moazed

(10) Patent No.: US 11,253,147 B1
(45) Date of Patent: Feb. 22, 2022

(54) OPHTHALMIC INSTRUMENT AND METHOD RELATING TO THE IRIS OF THE EYE

(71) Applicant: Kambiz Thomas Moazed, New York, NY (US)

(72) Inventor: Kambiz Thomas Moazed, New York, NY (US)

( * ) Notice: Subject to any disclaimer, the term of this patent is extended or adjusted under 35 U.S.C. 154(b) by 0 days.

(21) Appl. No.: 15/330,927

(22) Filed: Nov. 14, 2016

Related U.S. Application Data

(60) Provisional application No. 62/285,946, filed on Nov. 14, 2015.

(51) Int. Cl.
| | |
|---|---|
| *A61B 3/12* | (2006.01) |
| *A61B 3/10* | (2006.01) |
| *A61B 3/00* | (2006.01) |
| *A61B 3/14* | (2006.01) |
| *A61F 9/008* | (2006.01) |

(52) U.S. Cl.
CPC ............ *A61B 3/102* (2013.01); *A61B 3/0025* (2013.01); *A61B 3/1025* (2013.01); *A61B 3/14* (2013.01); *A61F 9/00804* (2013.01); *A61F 2009/00851* (2013.01); *A61F 2009/00876* (2013.01)

(58) Field of Classification Search
CPC ........... A61B 5/163; A61B 3/102; A61B 3/14; A61B 2090/3735; A61B 3/0008; A61B 3/1005; A61B 5/0066; A61B 5/0073; A61B 3/13; A61B 3/10
USPC .................. 351/206, 246, 205, 221, 212
See application file for complete search history.

(56) References Cited

U.S. PATENT DOCUMENTS

| | | | | |
|---|---|---|---|---|
| 9,125,593 | B2 * | 9/2015 | Isogai | A61B 3/0058 |
| 2012/0083667 | A1 * | 4/2012 | Isogai | A61B 3/102 |
| | | | | 600/300 |
| 2013/0188140 | A1 * | 7/2013 | Bagherinia | A61B 3/102 |
| | | | | 351/206 |
| 2014/0268039 | A1 * | 9/2014 | Arianta | A61B 3/14 |
| | | | | 351/206 |
| 2015/0042949 | A1 * | 2/2015 | Jeglorz | A61B 3/102 |
| | | | | 351/206 |

OTHER PUBLICATIONS

Abstract, Sheh et al., Diagnostic Potential of Iris Cross-sectional Imaging in Albinism Using Optical Coherence Tomography, Ophthalmology, Oct. 2013, 2082-2090, 120/10.
Sheh et al., Diagnostic Potential of Iris Cross-sectional Imaging in Albinism Using Optical Coherence Tomography, Ophthalmology, Oct. 2013, 2082-2090, 120/10.
Jacob, 2010. Fourier domain pump-probe optical coherence tomography imaging of Melanin.
Skalet, 2015. A pilot study of OCT angiography of iris melanomas. [ABSTRACT].

* cited by examiner

*Primary Examiner* — Hung X Dang
(74) *Attorney, Agent, or Firm* — David M. McConoughey

(57) ABSTRACT

A system and a method may be provided relating to the iris of an eye based on three-dimensional image data acquired by an optical coherence tomography.

8 Claims, 2 Drawing Sheets

| NEW |
|---|
| a light source for generating a beam of light; |
| a scanner for directing the beam to different locations at <u>the stroma of</u> the iris within the eye; |
| a detector for collecting 3D image information relating to <u>the stroma of</u> the iris; and |
| a processor for processing information about <u>the stroma of</u> the iris based on an analysis of the 3D image information. |

| ORIGINAL |
| Information Processing Assembly |
| Camera with OCT |
| Iris of the Eye |

Fig. 1

| NEW |
|---|
| a light source for generating a beam of light; |
| |
| a scanner for directing the beam to different locations at <u>the stroma of</u> the iris within the eye; |
| |
| a detector for collecting 3D image information relating to <u>the stroma of</u> the iris; and |
| a processor for processing information about <u>the stroma of</u> the iris based on an analysis of the 3D image information. |

Fig. 2

OPHTHALMIC INSTRUMENT AND METHOD RELATING TO THE IRIS OF THE EYE

CROSS-REFERENCE TO RELATED APPLICATIONS

Benefit of the priority of U.S. Patent Application Ser. No. 62/285,946, filed Nov. 14, 2015 is hereby claimed.

STATEMENT REGARDING FEDERALLY SPONSORED RESEARCH OR DEVELOPMENT

Not applicable.

THE NAMES OF THE PARTIES TO A JOINT RESEARCH AGREEMENT

Not applicable.

REFERENCE TO A SEQUENCE LISTING

Not applicable.

BACKGROUND OF THE INVENTION

Field of the Invention

The present invention relates to a method and a system for providing Optical Coherence Tomography information relating to the iris of an eye.

Background

In recent years the development of Optical Coherence Tomography (OCT) has become a valuable non-invasive imaging technique for evaluation, diagnosis and treatment of ocular tissue disorders. Originally, it was developed to evaluate the retina and also to evaluate and follow the course of diseases, such as macular degeneration and macular edema), and has extended to optic nerve head OCT for glaucoma evaluation, and evaluation of the cornea and anterior segment, including the angle structure. OCT is also used for cataract surgery for invasive programmed laser dissection with Femto laser.

Until now there has been no attention to focus on histological structure and anatomy of the iris. Images that exist of the anterior segment OCT of the iris are very crude and primitive.

BRIEF SUMMARY OF THE INVENTION

In accordance with the present invention, a method and a system may be provided relating to the iris of an eye based on three-dimensional image data acquired by an optical coherence tomography.

In accordance with the present invention, the method comprises the steps of:
 a. Acquiring three-dimensional image information related to the iris by an optical coherence tomography; and
 b. Processing said information.

Further in accordance with the present invention, the optical coherence tomography system comprises:
 a. a light source for generating a beam of light;
 b. a scanner for directing the beam to different locations at the iris within the eye;
 c. a detector for collecting 3D image information relating to the iris;
 d. a processor for processing information about the iris based on an analysis of the 3D image information.

BRIEF DESCRIPTION OF THE SEVERAL VIEWS OF THE DRAWINGS

FIG. 1 is a flow diagram of a method in accordance with the present invention and FIG. 2 is a diagram of a system in accordance with the present invention.

DETAILED DESCRIPTION OF PREFERRED EMBODIMENTS OF THE INVENTION

In accordance with the present invention, a method and a system may be provided displaying information related to the iris of an eye based on three-dimensional image data acquired by an optical coherence tomography system.

In accordance with the present invention, the method comprises the steps of:
 a. identifying information related to the iris based on an analysis of the image data; and
 b. displaying an image illustrating said information related to the iris.

In accordance with the present invention, the optical coherence tomography system comprises:
 a. a light source for generating a beam of light;
 b. a scanner for directing the beam to different locations at the iris within the eye;
 c. a detector for collecting 3D image information about the reflectance distribution at the iris within the eye;
 d. a processor for identifying information about the iris based on an analysis of the 3D image information; and
 e. a display for displaying an image illustrating said information about the iris.

There are specific and unique properties of the iris that makes it very different from the other parts of the eye and—as the consequence—different from Optical Coherence Tomography of the other parts of the eye.

Today's common uses of OCT of ocular tissue are focused on
 1. optic nerve to evaluate glaucoma
 2. retina in diabetic evaluation
 3. macula for macular degeneration or edema
 4. the lens for femto-assisted cataract surgery and
 5. the anterior chamber for evaluation of cornea and angle structures.

All these parts of the eye have very standard and similar structures and layers which can be easily traced by specific-designed software.

The iris is the only part of the eye that is completely different and unique in each individual person that makes it more challenging to evaluate the iris by Optical Coherence Tomography. (This is so completely different and unique in each individual person, that it is to the point that the iris is used in security systems and banks to identify individuals.)

At least a few of these structural differences can be summarized as follows:
 1. Iris shape,
 2. Iris thickness,
 3. Anterior surface folds and craters (Crypts of Fuchs, collarette, Folds of Schwalbe, etc.),
 4. Collagen content and distribution,
 5. Anterior surface structure (Fibroblasts and melanocytes intermingling),
 6. Melanin content of the anterior surface (The eye color), 7. Melanin content of the iris stroma (The eye color),
8. Vascular structure and their pigment component,
9. Iris nevus and moles, and
10. Other irregularities and defects.

These structural changes require an OCT system able to adjust to all these varieties and differences of structure and contents in order to be able to specifically identify the tissue structural varieties among other things as enumerated above. As the result, it is of great value to identify and treat diseases and anomalies of the iris.

For example, one of the common problems in using current available OCT units, is the scattering properties of melanin. For example, in blue eyes there is no pigment melanin in the anterior surface of the Iris which is different from brown or very dark eyes that contain pigment melanin in all layers of the stroma.

There is a need for high Speed Spectral Domain OCT (SD-OCT) to capture data from the constantly moving iris (The movement can be minimized by using Pilocarpine eye drops 15 minutes before the scanning).

Iris OCT provides cross-sectional visualization of iris tissue, iris morphology, melanocyte concentration and location the sphincter muscle, inflammatory cells and posterior Iris Pigment Epithelium (IPE).

Since anterior segment OCT (AS-OCT) was introduced in 2006, clinicians have frequently used it to gather data for a multitude of patient presentations AS-OCT has been useful for evaluating post-penetrating keratoplasty eyes with secondary glaucoma, after laser iridotomy and after cataract surgery. AS-OCT has also been used to visualize the position and patency of aqueous shunt devices in the anterior chamber that corneal edema may partially obscure.

AS-OCT penetrates full thickness iris lesions and allows three-dimensional measurement of lesion size. Compared to slit-lamp photography and ultrasound biomicroscopy, AS-OCT is helpful in evaluating iris tumors, including focal iris nevus, diffuse iris nevus, amelanotic iris nevus, iris melanocytosis and iris melanoma.

Three dimensional OCT has been discussed also in the following article: https://www.osapublishing.org/view_article.cfm?gotourl=https%3A%2F%2Fwww%-2Eosapublis hing%2Eorgo%2FDirectPDFAccess%2FB1D-A65C0%2D9A5F%2DADC7%2D704F1D06359908D3%5F86669%2Foe%2D13%2D26%2D10652%2Epdf%3Fda%3D1%26id%3D86669%26seq%3D0%26mobile%3Dno&org=

An object is to identify the exact plane (cellular layer) of pigment cells in the stroma of the iris with ultra-high resolution high speed OCT and aim it with femto laser in a specific depth and power to accomplish the color change that is desired by the patient. Random destruction of the melanocytes causes a white iris which is cosmetically unappealing. With a femto laser (that does not produce heat and possesses complete accuracy) the selected iris tissue layer can be limited to few microns on a specific plane. Computer software can calculate the location, thickness and depth of the ablation as desired.

In three-dimensional tomography, the galvano mirror for the B-scan is driven by a triangular wave. A B-scan trigger, which is synchronously generated for each B-scan, is as an update clock of C-sc. Due to the fact an, and the C-scan trigger initiates spectral detection. Complete spectral signals and A-triggers for a single C-scan are stored in the on-board memory Three of the A/D board, then transferred to the main memory of a PXI PC unit after the measurement, and finally stored on a hard disk. The stored data is loaded during the post-processing process, and arranged into a three-dimensional spectral signal by using the A-scan triggers, this is followed by the application of the above-mentioned signal processing. A typical C-scan comprises 200 B-Scans, each of which comprises 200 A-scans. Hence, the volume size is 200×200×1024 voxels and the acquisition time is 2 s·al Optical Coherence Tomography generates cross sectional images by analyzing the time delay and magnitude change of low coherence light as it is backscattered by ocular tissues. An infrared scanning beam is split into a sample arm (directed toward the subject) and a reference arm (directed toward a mirror). As the sample beam returns to the instrument it is correlated with the reference arm in order to determine distance and signal change via photodetector measurement. The resulting change in signal amplitude allows tissue differentiation by analysis of the reflective properties, which are matched to a false color scale. As the scanning beam moves across tissue, the sequential longitudinal signals, or A-scans, can be reassembled into a transverse scan yielding cross-sectional images, or B-scans, of the subject. The scans can then be analyzed in a variety of ways providing both empirical measurements (e.g. RNFL or retinal thickness/volume) and qualitative morphological information. Coherence Tomography generates cross sectional images by analyzing the time delay and magnitude change of low coherence light as it is backscattered by ocular tissues. An infrared scanning beam is split into a sample arm (directed toward the subject) and a reference arm (directed toward a mirror). As the sample beam returns to the instrument it is correlated with the reference arm in order to determine distance and signal change via photodetector measurement. The resulting change in signal amplitude allows tissue differentiation by analysis of the reflective properties, which are matched to a false color scale. As the scanning beam moves across tissue, the sequential longitudinal signals, or A-scans, can be reassembled into a transverse scan yielding cross-sectional images, or B-scans, of the subject. The scans can then be analyzed in a variety of ways providing both measurements (e.g. RNFL or retinal thickness/volume) and qualitative morphological information.

Optical Coherence Tomography generates cross sectional images by analyzing the time delay and magnitude change of low coherence light as it is backscattered by ocular tissues. An infrared scanning beam is split into a sample arm (directed toward the subject) and a reference arm (directed toward a mirror). As the sample beam returns to the instrument it is correlated with the reference arm in order to determine distance and signal change via photodetector measurement. The resulting change in signal amplitude allows tissue differentiation by analysis of the reflective properties, which are matched to a false color scale. As the scanning beam moves across tissue, the sequential longitudinal signals, or A-scans, can be reassembled into a transverse scan yielding cross-sectional images, or B-scans, of the subject. The scans can then be analyzed in a variety of ways providing both empirical measurements (e.g. RNFL or retinal thickness/volume) and qualitative morphological information.

Due to the fact that melanin pigment stores zinc can be used as contrast in iris.

Examples of diseases of the iris that can benefit from the system and method of the present invention are:
  a. Iris melanoma (cancer of pigmented cells of the iris),
  b. Iritis (inflammation of the iris),
  c. Bechet's Disease,
  d. Iris neovascularization,
  e. Metastatic tumors of the iris,
  f. Diabetic neovascular glaucoma,
  g. Lupus, and
  h. Radiation induced complications.

For the above reasons there is a need for a system and a method that can safely and efficiently deliver the desired treatment agents with high concentration and many substances are suitable for delivery by contact to the iris surface.

OCT in conjunction with suitable software provide direct optical microscopy in:
 a. Studying the structure of the iris,
 b. Identifying and diagnosing abnormalities and diseases of the iris.
 c. Iris lesions.
 d. Metastatic tumors and Malignant Melanoma of the iris.
 e. Identifying and diagnosing Pigmentary glaucoma.
 f. Monitoring the course of treatment of the acute and chronic Anterior Uveitis which is a very common condition and difficult to treat.
 g. Identifying the population, melanin density, anatomical location of melanocytes in the iris, for possible cosmetic intervention with different modalities such as laser, small molecules, etc.

Structure of the Iris.

Due to the fact that there is a vast diversity of the structure of the iris in humans. the iris OCT of the present invention can be used to study these differences and categorize and use them as identification tools, and for security purposes.

Detection of early iris neovascularization with OCT in diabetic patients can prevent blindness due to the grave situation that is called "Rubeosis Irides." This can be reversed by heavy pan retinal photocoagulation of the retina.

Detection can be through: Doppler Fourier Domain Optical Coherence Tomography.

Diagnosis can be through: Early diabetic angle neovascularization is serious and usually causing blindness in diabetic patients. Early diabetic angle neovascularization (New vessels start to grow at the angle of the eye at the junction of iris periphery to the cornea. The angle is where the drainage system of the eye is located which the aqueous humor (The water in the eye) is getting absorbed back to the blood circulation. As the new vessels contract due to physiologic property of any new vessel growth, it will retract and close the angle of the eye. As a result the aqueous fluid that enters the eye by leakage from ciliary body behind the pupil, cannot exit and increases the intra-ocular pressure which causes the destruction of the optic nerve due to high pressure. As the result causes blindness. a serious and usually irreversible condition in diabetic patients.

Treatment. There is no medical treatment. Surgical treatment is available through laser surgery. Pan retinal laser photocoagulation will reverse the progression of the disease. In pan retinal laser photocoagulation, a contact lens is placed in the front of the eye and by using argon laser transferring laser energy to cause the heat induced burned on the retina and choroid layers of the eye. Interestingly the burns on the retina cause the iris new vessels to stop growing and stop the invasion and even reversal of angle closure. A special contact lens made only for laser surgery to focus and direct the laser beam to the exact desired location.

Detection of iris thinning and atrophy in pigmentary glaucoma can be Detected by Swept-Source Optical Coherence Tomography that reveals calculates the Iris Volume and can be can be reversed by YAG laser iridotomy, which prevents blindness due to high intraocular pressure. Detect is by swept-source anterior segment optical coherence tomography (SS-ASOCT). Diagnosis is for pigmentary glaucoma. Pigmentary glaucoma is a condition that is associated with iris atrophy and thinning. The iris moves back and forth and releases the pigment which clogs the meshwork the drains the Aqueous Humor from the eye and increases the intraocular pressure that causes damage to the optic nerve. Medical treatment is by prostaglandin analogues and pilocarpine. Prostaglandin analogues decreases intraocular pressure and pilocarpine by making the pupil small pulls the iris away from the lens and decreases the release of the pigment. Surgical treatment is by laser iridotomy. Using Argon or YAG laser is very beneficial to make a small hole in the iris to make a new connection between anterior and posterior chamber of the eye. This is done by placing a contact lens in front of the eye and direct the laser energy to destroy the tissue of the iris either by heats as in Argon laser or by plasma formation with YAG laser to induce a 1 millimeter full thickness hole in the body of the iris. Special contact lens made only for laser surgery to focus and direct the laser beam to the exact desired location.

Abnormalities and Diseases of the Iris.

OCT with molecular contrast ability can identify and diagnose congenital abnormalities, such as colobomas, aniridia and albinism and genetic anomalies, such as Waardenburg Syndrome, PAX6, and Forkhead box C1

Even though there are no treatments available, the conditions can be monitored and handled more properly with OCT in accordance with the present invention. OCT of the above conditions has not been established and categorized. Specific anomalies to be categorized in each condition by fast high resolution OCT. for example Waardenberg Syndrome which has an incidence of 1/42,000 is a mutation in genes that that are responsible for pigment formation and as a result causes blue eyes, blond hair, deafness and white skin patches (vitiligo.) Detection identifies specific anomalies to be categorized in each condition by fast high resolution OCT. The diagnosis of each disease can be confirmed by genetic studies and by characterization of the anomalies by OCT. There is usually no medical treatment available. Surgical treatment and laser surgery may be indicated in special cases depending on the associated complications.

Iris Lesions.

Lisch nodules of Neurofibromatosis (multiple genetically inherited conditions that have different genetic and clinical presentations. They all share the formation of multiple benign tumor formations called Hamartomas. They have specific small tumors that form on the surface of the iris that helps to make the diagnosis. The characteristics of these lesions have not been described by one micron OCT yet. Lisch nodules appear among prepubertal children and are apparently unique to Neurofibromatosis. They are a valuable criterion by which to diagnose neurofibromatosis in problematic cases.

Doppler OCT can identify infiltrative histiocytic lesion of the iris, spontaneous hyphema (bleeding inside the eye) which is the characteristic of juvenile xanthogranuloma can be identified. Iris lesions in Juvenile Xanthogranuloma (JXG): This is an uncommon non-Langerhans cell histiocytic disorder that occurs predominantly in infants. Iris lesions that are due to accumulation of inflammatory cells that leads to spontaneous bleeding inside the eye and will cause blindness. This condition usually responds to topical steroid treatment which prevents blindness.

Iris lesions associated with Sarcoidosis also an important diagnostic tool in which one micron OCT can assist. "Koeppe/Busacca" specific nodules of Sarcoidosis. Sarcoidosis is a multi systemic granulomatous (Special type of inflammation) disease of unknown cause and unpredictable course. Eye and lungs are affected usually and iris lesions are very helpful to make a diagnosis which is a hard task to do otherwise.

One micron OCT with cellular and sub-cellular imaging capability may be used in evaluating the Iris lesions which are characteristics of certain systemic disease and can be helpful for making the correct diagnosis.

Malignancies

Iris malignant melanoma and also metastatic lung and breast cancer can manifest as iris tumors that can be diagnosed and monitored by OCT.

OCT with HD 3D ("three dimensional") planes would identify and map the extension and the invasion of the tumor in a live tissue and would be helpful to plan an excision accordingly.

Iris melanoma is usually in Caucasian patients and can be difficult to differentiate from iris nevus (mole). It can invade outside the eye by local infiltration or by seeding in the eye or metastasis to the other organs. Metastasis is 5% in 10 years. Treatment is variable from no surgery (observation) to block removal of the lesion or by radioactive implant and finally by removing the whole eyeball (Enucleation).

Identifying and Diagnosing Pigmentary Glaucoma.

Detection of iris thinning and atrophy in pigmentary glaucoma can be Detected by Swept-Source Optical Coherence Tomography that reveals calculates the Iris Volume and can be reversed by YAG laser iridotomy, which prevents blindness due to high intraocular pressure. Detect is by swept-source anterior segment optical coherence tomography (SS-ASOCT). Diagnosis is for pigmentary glaucoma. Pigmentary glaucoma is a condition that is associated with iris atrophy and thinning. The iris moves back and forth and releases the pigment which clogs the meshwork the drains the Aqueous Humor from the eye and increases the intraocular pressure that causes damage to the optic nerve. Medical treatment is by prostaglandin analogues and pilocarpine. Prostaglandin analogues decreases intraocular pressure and pilocarpine by making the pupil small pulls the iris away from the lens and decreases the release of the pigment. Surgical treatment is by laser iridotomy. Using Argon or YAG laser is very beneficial to make a small hole in the iris to make a new connection between anterior and posterior chamber of the eye. This is done by placing a contact lens in front of the eye and direct the laser energy to destroy the tissue of the iris either by heats as in Argon laser or by plasma formation with YAG laser to induce a 1 millimeter full thickness hole in the body of the iris. Special contact lens made only for laser surgery to focus and direct the laser beam to the exact desired location.

Detection of iris thinning and atrophy in pigmentary glaucoma can be Detected by Swept-Source Optical Coherence Tomography that reveals calculates the Iris Volume and can be reversed by YAG laser iridotomy, which prevents blindness due to high intraocular pressure. Detect is by swept-source anterior segment optical coherence tomography (SS-ASOCT). Diagnosis is for pigmentary glaucoma. Pigmentary glaucoma is a condition that is associated with iris atrophy and thinning. The iris moves back and forth and releases the pigment which clogs the meshwork the drains the Aqueous Humor from the eye and increases the intraocular pressure that causes damage to the optic nerve. Medical treatment is by prostaglandin analogues and pilocarpine. Prostaglandin analogues decreases intraocular pressure and pilocarpine by making the pupil small pulls the iris away from the lens and decreases the release of the pigment. Surgical treatment is by laser iridotomy. Using Argon or YAG laser is very beneficial to make a small hole in the iris to make a new connection between anterior and posterior chamber of the eye. This is done by placing a contact lens in front of the eye and direct the laser energy to destroy the tissue of the iris either by heats as in Argon laser or by plasma formation with YAG laser to induce a 1 millimeter full thickness hole in the body of the iris. Special contact lens made only for laser surgery to focus and direct the laser beam to the exact desired location.

Acute and Chronic Anterior Uveitis

Monitoring the course of treatment of acute and chronic Anterior Uveitis is a very common condition and difficult to treat. Idiopathic anterior uveitis is increasingly being associated with a viral etiology. Herpes simplex and Herpes zoster virus (HSV/HZV) are known causes of anterior uveitis but other viruses including Cytomegalovirus (CMV) and Rubella are now being recognized. Viral anterior uveitis has characteristic clinical features, an understanding of which assists the examining ophthalmologist in making an appropriate diagnosis and in initiation of a timely management which varies with the viral strain. The diagnosis may be relatively straight forward in the presence of concomitant skin lesions, active keratitis, and/or corneal anesthesia. However, in the absence of such clues, the diagnosis requires a high index of clinical suspicion and astute observations, especially as access to intraocular fluid analysis is not available to most clinicians.

Identifying the type of inflammatory cells with OCT would help the diagnosis and treatment with antiviral medications.

Pigmentation

OCT is useful in identifying the population, melanin density, and anatomical location of melanocytes in the iris, for possible cosmetic intervention with different modalities for normal to malignant pigmentary changes and intervention with other modalities such as laser, small molecules, etc. There will be many essential uses for identifying the pigmentation of the iris. The amount of melanin pigment on the surface of the iris and in the stroma (the body) of the iris is directly associated with the color of the eye. There are many factors involved in the appearance of the iris color but the most prominent and most important of all is the reflection of the full spectrum of the light after bouncing out form the iris. The collagen on the body and surface of the iris absorbs the red component of the spectrum and only the blue portion reflects back which gives the illusion that the iris is blue to the observer. In the presence of melanin the full spectrum also gets absorbed and causes a variety of different colors according to the amount, the depth, and the location of the melanin pigment in the iris. If there is no pigment on the surface of the iris, the eye looks blue. If there is minimal pigment, it would look green. With more melanin and it looks from hazel to light brown to dark brown and black (almost black.)

OCT is crucial to locating the amount and three-dimensional location of the melanin pigment in the iris if there is to be any means of intervention to change the color of the eye (which can be from chemicals to ultrasound or laser or nanoparticles or biological colors and adhesives to plates or disc implants to be delivered to the iris.)

A software program can be stablished to calculate the amount and three-dimensional location of the pigment from OCT information and then calculating the amount of pigment that should be eliminated to achieve the desired color of the eye accordingly. A pre-set color matching capability with consideration of different variables such as concentration of melanin molecules (which can be a combination of eumelanin and pheomelanin), 3D mapping of the pigments, topography of iris structure would be held in a database for comparison and calibration.

The anatomy of the iris also has influence on the color of the iris. The amount of blood vessels, the thickness of the supporting connective tissue, and the amount of transparent collagen fibers on the surface of the iris can be all documented by a hi resolution OCT scanner.

The foregoing components can be attached to a femto laser system to eliminate the pigment cells according to the software calculation and patient's desired color. This combination is similar to that used for cataract surgery in which OCT maps the anterior segment and the eye, then software calculates the desired areas for cutting as instructed by the eye surgeon, and then a femto laser system does the cutting while the eye is covered with a suction cup filled with balanced salt saline.

With respect to all of the foregoing embodiments and as shown in FIG. 1, a high definition/high resolution camera with high speed OCT collects information from the iris of the patient. Suitable software recognizes the anomalies in the information thus obtained by comparing that information to a database of standard values. Proposed diagnosis would be determined by software. Then, software proposes a recommended mode of action and genetic or other testing may be requested. Finally, the recommended mode of action can be implemented by interaction with robotic tools with the iris of the patient.

I claim:

1. A method comprising the steps of:
   acquiring three-dimensional image information related to the stroma of the iris by optical coherence tomography; and
   processing said information.
2. A method in accordance with claim 1 wherein
   said three-dimensional image information related to the stroma of the iris comprises one or more of the following information,
   a. Anterior surface folds or craters or both surface folds and craters,
   b. Collagen content or distribution or both content and distribution,
   c. Anterior surface structure,
   d. Melanin content of the anterior surface,
   e. Melanin content of the iris stroma.
3. A method in accordance with claim 2 wherein anterior folds or craters or both surface folds and craters comprise
   a. Crypts of Fuchs,
   b. collarette,
   c. Folds of Schwalbe or a combination thereof.
4. A method in accordance with claim 2 wherein said anterior surface structure comprises fibroblasts and melanocytes intermingling.
5. An optical coherence tomography system comprising:
   a light source for generating a beam of light;
   a scanner for directing the beam to different locations at the stroma of the iris within the eye;
   a detector for collecting 3D image information relating to the stroma of the iris; and
   a processor for processing information about the stroma of the iris based on an analysis of the 3D image information.
6. A system in accordance with claim 5 wherein said three-dimensional image information related to the stroma of the iris comprises one or more of the following information,
   a. Anterior surface folds or craters or both surface folds and craters,
   b. Collagen content or distribution or both content and distribution,
   c. Anterior surface structure,
   d. Melanin content of the anterior surface,
   e. Melanin content of the iris stroma.
7. A method in accordance with claim 6 wherein... comprises
   a. Crypts of Fuchs,
   b. collarette,
   c. Folds of Schwalbe or a combination thereof.
8. A method in accordance with claim 6 wherein
   Anterior surface structure comprises fibroblasts and melanocytes intermingling.

* * * * *